United States Patent [19]

Samour et al.

[11] Patent Number: 5,344,941
[45] Date of Patent: Sep. 6, 1994

[54] WATER SOLUBLE SALTS OF THIONAPHTHENE-2-CARBOXYLIC ACID

[76] Inventors: Carlos M. Samour, 254 Ocean Ave., Newport, R.I. 02840; Stefanos Daskalakis, 116 Early St., Harrison, N.J. 07960; James R. Marshall, 7 B Old Colony Dr., Westford, Mass. 01886

[21] Appl. No.: 987,993

[22] Filed: Dec. 9, 1992

Related U.S. Application Data

[63] Continuation of Ser. No. 739,779, Jul. 31, 1991, abandoned, which is a continuation of Ser. No. 86,848, Aug. 19, 1987, abandoned, which is a continuation-in-part of Ser. No. 903,385, Sep. 3, 1986, abandoned.

[51] Int. Cl.$^5$ ............................................. C07D 333/56
[52] U.S. Cl. ....................................................... 549/57
[58] Field of Search ........................... 549/57; 514/443

[56] References Cited

U.S. PATENT DOCUMENTS

| | | | |
|---|---|---|---|
| 4,101,668 | 7/1978 | Samour et al. | 514/443 |
| 4,125,621 | 11/1978 | Samour et al. | 514/443 |
| 4,185,108 | 1/1980 | Samour et al. | 514/419 |
| 4,434,163 | 2/1984 | Lombardino | 514/222 |

Primary Examiner—Patricia L. Morris
Assistant Examiner—Jacqueline Haley
Attorney, Agent, or Firm—Sherman and Shalloway

[57] ABSTRACT

Lysine and arginine salts of thionaphthene-2-carboxylic acid (TNCA) are disclosed. These compounds are useful as treatments for osteoporosis and exhibit an increased water solubility.

3 Claims, No Drawings

WATER SOLUBLE SALTS OF THIONAPHTHENE-2-CARBOXYLIC ACID

This Application is a Continuation of application Ser. No. 07/739,779, filed Jul. 31, 1991, abandoned, which in turn is a Continuation of application Ser. No. 07/086,848, filed Aug. 19, 1987, abandoned, which in turn is a Continuation in part of application Ser. No. 06/903,385, filed Sep. 3, 1986, now abandoned.

This invention relates to thionapthene-2-carboxylic acid (TNCA) water-soluble salts (TNSA) (Also called Benzo(b)thiophene-2-carboxylic acid salts), and processes of making and using these compounds.

BACKGROUND OF THE INVENTION

Osteoporosis is a common and progressive condition occurring in adults which results in a decrease in bone throughout the body. This loss includes the mineral portion of the bone, which is a calcium phosphate material called "hydroxyapatite", as well as the matrix, which is a protein called "collagen". Osteoporosis may begin in early adulthood and progress, inexorably, to middle age and old age with manifestations running the gamut of moderate to severe pain along with X-ray evidence of bone loss and/or deformation to eventual brittleness which we see evidenced, for example, in older people who so easily break a hip bone from a simple, and seemingly not dangerous, fall. It has been stated that osteoporosis is the most common cause of fractures in people over the age of 65.

While the causes of osteoporosis are not well understood and, in many cases quite obscure, it is believed that there is an imbalance between bone production and bone resorption (i.e., bone breakdown).

During the life of an animal, new bone is continuously being formed and old bone resorbed. In osteoporosis, resorption exceeds bone formation.

Present methods for treating osteoporosis are far from satisfactory. Such treatments include the administration of calcium salts, fluorides, calcitonin, estrogens, Vitamin D, and anabolic agents, among others. Anabolic agents and estrogen therapy have been the therapy of choice for osteoporosis in post-menopausal women. Such treatments appear to entail an increased risk of uterine and breast cancer. Other treatments still remain to be proven including the Physical Therapy approach.

Among the newer approaches to the treatment of osteoporosis has been the use of materials with hypocalcemic activity, i.e., lowering of the serum calcium, which is believed to be related to and indicative of a decrease in the rate of bone resorption. Calcitonin, mithramycin (an antibiotic) and certain phosphonates are representative hypocalcemic agents, but adverse effects and lack of effectiveness in bone-loss prevention associated with the use of such agents, make continued research necessary.

In recent U.S. Pat. Nos. 4,101,668 (issued Jul. 18, 1978), 4,125,621 (issued Nov. 14, 1978) and 4,185,108 (issued Jan. 22, 1980), all three having as inventors C. M. Samour and J. A. Vida, there are disclosed a wide variety of benzo-heterocyclic compounds for use as antiosteoporotic agents. Among the specific compounds described are thionaphthene-2-carboxylic acid, thionaphthene-3-carboxylic acid, thionaphthene-4-carboxylic acid, dibenzothiophene-4-carboxylic acid, thioxanthene-9-one-4-carboxylic acid and indole-2-carboxylic acid.

The compounds are compared to thyrocalcitonin (TCT), the latter, a bond-remodeling hormone which is capable of reducing bone resorption rates. In the patented disclosures, the effectiveness of any bone resorption modifying agent is determined by measuring the effect on the production of cyclic adenosine-3'5'-monophosphate (c-AMP) using the methods of Rodan et al, J.B.C. Vol 429, page 306, 1974; Rodan et al, Science, Vol. 189, page 467, 1975. In the comparison, the activity shown by the free acid compounds covered by the disclosure of the aforementioned patents ranges from slightly more than half as effective to twice as effective as TCT in stimulating the production of c-AMP.

Prior Art

The U.S. Pat. Nos. (to Samour et al) 4,101,668, 4,125,621 and 4,185,108 mentioned in the "Background" to the present invention constitute the only significant Prior Art to which we are aware.

In the patents, mention is made that the "pharmaceutically acceptable salts include the non-toxic metallic salts such as sodium, potassium, calcium and aluminum, the ammonium salt and substitued ammonium salts, e.g., salts of such nontoxic amines as trialkylamines including thiethylamine "—(presumably triethylamine is intended)—" L-lysine, procaine, dibenzylamine, N-benzyl-beta phenylethylamine, L-ephenamine-N,N' dibenzylethylenediamine, N-(lower) alklypiperidine, e.g., N-ethylpiperidine", but no specific salt is given. The studies shown in the patent were done in vitro and in vivo but the latter were conducted by injecting the drug. In Example 5 of each patent, benzo(b)thiophene-2-carboxylic acid was used for 3 days (1 mg/day by subcutaneous (S.C.) injection. In Example 6 the dose was reduced to 200 ug/day and in Example 7, the drug was injected for 10 days (S.C. 1 mg/day).

In other studies it has been found that in acute toxicities in rats and monkeys, using TNCA in gum tragacanth, the oral $LD_{50}$ in mice is 3.6 g/kg whereas when injected subcutaneously, the oral $LD_{50}$ in mice is 1.45 g/Kg, indicating a low response level to the orally ingested drug.

DESCRIPTION OF THE PRESENT INVENTION

The present invention provides new salts of benzo(b)-thiophene-2-carboxylic which are readily prepared in high yields, which are particularly free of irritating side effects in the stomach as well as other untoward effects when taken orally, and which give rise to rapid and clinically-response-effective blood levels via the oral route. The $LD_{50}$ of the water-soluble salts of this invention and particularly the L-lysine salt when given orally is almost equivalent to that obtained when administered intraperitoneally.

The specific salts with which this invention is concerned are the L-lysine salt, the triethanolamine salt, the ammonium salt, the piperidine salt, and the L-arginine salt.

Surprisingly, these salts are easily prepared, readily isolated, obtainable in good yields, and water-soluble. This is to be contrasted with other salts which would suggest themselves, namely, the sodium salt, potassium salt, glycine salt, L-alanine salt, L-proline salt and even the triethylamine salt. As a matter of fact so suggestive a salt as the potassium and sodium salts have proven difficult to prepare and when made are mainly insoluble in water. In this regard, it is to be noted that while the ammonium salt is simply and conveniently made by merely mixing even dilute ammonium hydroxide solutions with the solid free acid (benzo(b)thiophene-2-carboxylic acid) and evaporating the water to isolate the ammonium salt, solid TNCA when mixed into aqueous caustic soda solutions is totally unaffected and unreactive to form the sodium salt; this is true with 8% (2N) and with 20%, 40%, and 60% aqueous solutions. This is also the case when one uses aqueous sodium carbonate. Considering that the pK of the TNCA is 3.4, this action is quite strange. The L-lysine salt is also made in the same simple and efficacious manner as the ammonium salt, again by the incremental addition of the TNCA to an aqueous solution of L-lysine. The use of solutions of both reactants in a suitable solvent such as methanol may be used with facility since the TNCA compound is soluble in methanol. In contrast, the sodium salt is produced only when one utilizes sodium ethoxide in methanol or sodium hydroxide in a mixture of alcohol and water. The formation of the sodium salt was demonstrated by means of infra-red spectroscopy and also the fact that it does not melt. Similarly, the potassium salt could not be formed by treatment with aqueous potassium hydroxide. However, the potassium salt of TNCA is formed when excess potassium hydroxide and TNCA are added to a warm solution of methanol containing a small amount of water.

The utility of the salts, in a clinical treating sense, is equivalent to TNCA itself but they are far more useful, practically, for the reasons of amelioration of side effects and the high blood levels available via the oral route.

As examples, TNCA, as an acid in high concentrations, causes gastric irritation, resulting in vomiting and bleeding. On the other hand, TNCA lysine salt acts as an effective buffer, hence prevents the adverse effects associated with gastric irritation.

More importantly, TNCA is poorly absorbed from the gastrointestinal tracts; as mentioned earlier, the oral LD$_{50}$ is 3.6 gm/Kg., whereas by injection, this value is only 1.45 g/Kg. In marked contrast, the oral dose of the TNCA lysine salt is roughly 1.5 g/Kg and, by injection, is not significantly different (approximately 1.3 g/Kg). This finding that TNCA lysine salt is equally effective when given orally or by injection, indicates that the lysine salt, in contrast to TNCA, is readily absorbed following oral administration.

The following examples will serve to illustrate the present invention without being deemed limitative thereof. Parts, when used, are by weight, unless otherwise indicated.

EXAMPLE 1

Preparation of Benzo(b)thiophene-2-carboxylic acid L-Lysine salt:

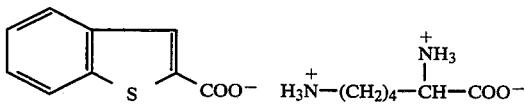

95.02 g (0.65 mole) of L-lysine is dissolved in 637 ml. of water. To this solution is added, in small portions, 115.83 g (0.65 mole) of TNCA (m.p. 237°–238° C.) and the reaction mixture is stirred at 50° C. for one hour. The mixture is then filtered and the water is removed from the filtrate to give a pinkish white solid of the above formula and with a melting point of 240°–242° C. The salt is highly (70%) water-soluble. A 5% aqueous solution of the salt has a pH of 5.75. It is insoluble in methyl alcohol, ethyl alcohol and toluene.

EXAMPLE 2

Preparation of the Triethanolamine salt:

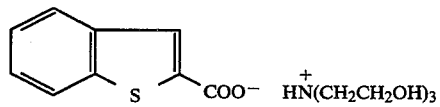

A solution is prepared by mixing a solution of 447 mg of triethanolamine (0.003 mole) in 15 ml of methanol with another solution of 537 mg (0.003 mole) benzo(b)-thiophene-2-carboxylic acid (TNCA) in 5 ml of methanol. The solution is filtered and the solvent is removed from the filtrate to give 850 mg of a white water-soluble solid, m.p.=144°–148° C. A 5% aqueous solution of the salt has a pH of 6.77.

EXAMPLE 3

Preparation of the Ammonium salt of TNCA

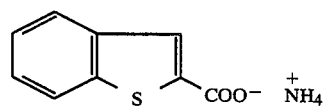

Following Example 1, 358 mg (0.002 mole) of TNCA in 10 ml of methanol is mixed with 2 ml of aqueous hydroxide (NH$_3$ content 28–30% in 1 ml of methanol). 327 mg of a white water-soluble solid, m.p.=247°–250° C. is obtained. A 5% aqueous solution of the salt as a pH of 6.05.

EXAMPLE 4

Preparation of the Arginine salt of TNCA

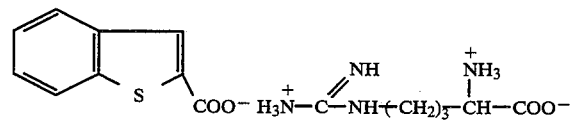

To a solution of 2.97 g (0.016 mole) of L-arginine in 18 ml of water is added, while being stirred, 3 g (0,016 mole) solid TNCA. The mixture is stirred at 40° C. until all TNCA dissolves. The water was removed in vacuum. 5.6 g of a white, water-soluble solid, m.p.=55°–60° C., is obtained. A 5% aqueous solution of the salt has a pH of 5.8. The salt is also soluble in methanol and ethanol.

EXAMPLE 5

Preparation of the Piperidine salt of TNCA

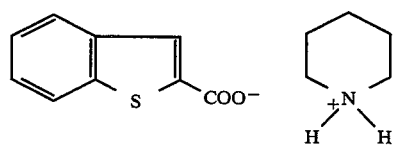

Following Example 1, 171 mg (0.002 mole) of piperidine in 4 ml methanol is mixed with 358 mg (0.002 mole) of TNCA in methanol. 367 mg. of a white moderately water-soluble solid was obtained, m.p.=122°−125° C. A 5% aqueous solution of the salt has a pH of 6.4.

EXAMPLE 6

Preparation of the Sodium salt of TNCA

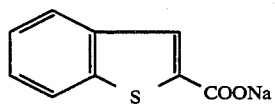

108 mg (0.002 mole) of sodium ethoxide in 6 ml methanol is mixed with 358 mg (0.002 mole) of TNCA in 10 ml of methanol. 321 mg of a white water-insoluble salt is obtained on removal of the methanol from the almost clear solution. The solid does not melt below 300° C. and the IR spectrum clearly indicates the presence of a salt.

EXAMPLE 7

Following the procedure of Example 6, 203 mg (0.002 mole) of triethylamine is dissolved in 4 ml of methanol and mixed with 358 mg (0.002 mole) of TNCA in 10 ml. of methanol. A water-insoluble liquid results.

EXAMPLE 8

Following the procedure of Example 1, L-alanine, L-glycine, and L-proline are used, in equivalent amounts in place of L-lysine. No water-soluble reaction product is formed.

The following tables (Experiments I and II) illustrate the effectiveness of the present invention in reducing the blood calcium levels of rats made hypercalcemic by the injection of Leydig-cell carcinoma-tumor material. For details of the methodology employed in these studies, see: Johannesson et al., Endocrinology 117/4: 1508–1511 (1985). Normal calcium blood levels are in the range of 9–10 mg/dL.

TABLE I

| | Calcium Serum Concentrations (Experiment 1) | | | |
|---|---|---|---|---|
| Measure | Group | N | Mean | S.D. |
| Initial | Control | 5 | 11.22 | 1.68 |
| Calcium | 195 mg/kg | 8 | 12.28 | 1.71 |
| Levels | 292 mg/kg | 9 | 13.31 | 3.32 |
| Final | Control | 5 | 17.38 | 3.71 |
| Calcium | 195 mg/kg | 8 | 14.85 | 3.56 |
| Levels | 292 mg/kg | 9 | 11.54 | 2.54 |

TABLE II

| | (Experiment 2) | | | |
|---|---|---|---|---|
| Measure | Group | N | Mean | S.D. |
| Initial | Control | 6 | 15.17 | 2.26 |
| Calcium | 195 mg/kg | 6 | 14.07 | 2.33 |
| | 292 mg/kg | 6 | 14.68 | 2.56 |
| | 389 mg/kg | 10 | 13.80 | 2.70 |
| Final | Control | 6 | 18.03 | 2.14 |
| Calcium | 195 mg/kg | 6 | 13.27 | 2.07 |
| Levels | 292 mg/kg | 6 | 11.00 | 1.30 |
| | 389 mg/kg | 8 | 10.16 | 0.49 |

The data in Tables I & II show that the initial serum concentrations of calcium are considerably higher than normal for the rat, ranging from 11.22 to 13.31 mg/dL (mg per deciliter) in Experiment 1 and from 13.80 to 15.17 mg/dL in Experiment 2. In the table, n=number of rats evaluated at each dosage and in controls while S.D.=standard deviation. These higher initial values reflect Leydig cell-induced hypercalcemia. Data for final calcium levels show the decreases in calcium levels produced following administration of the lysine salt of TNCA. Such decreases are clearly does-related in both experiments, dropping from control values of 17.38 to 11.54 in Experiment 1, and from 18.03 to 10.16 in Experiment 2, corresponding to doses of 292 mg/Kg and 389 mg/Kg, respectively. It is noteworthy that the serum calcium levels following treatment with the lysine salt of TNCA returned to pretreatment levels, but not to below normal values, i.e., not below calcium concentrations present before the development of Leydig cell tumors. This indicates that the lysine salt of TNCA is anti-hypercalcemic, rather than hypocalcemic. The distinction is important since the objective of therapy with this drug is to lower calcium significantly, but not to levels that would cause the adverse effects of hypocalcemia.

Particularly useful for patient use are pharmaceutically acceptable liquid dosage forms incorporating TNCA and they may be prepared by utilizing the teachings exemplified above regarding the formation of salts of TNCA with TNCA as the acid. The base may be chosen from the class of lysine, arginine, ammonium hydroxide, piperidine, and triethanolamine.

Liquid dosage forms may be prepared either by the dissolution of the isolated salt into water, by the dissolution of TNCA into an aqueous solution containing lysine, arginine, triethanolamine, piperidine, or ammonium salts, or by the simultaneous dissolution of TNCA and the free base into an aqueous medium.

The following are suggested dosage formulations:

In the liquid oral dosage form, one ml of the solution may contain 15–1000 mg of TNCA, as the salt of lysine, arginine, triethanolamine, piperidine, and/or ammonium hydroxide. Also contained in the solution may be sodium chloride for the purpose of achieving isotonicity, sodium hydroxide for pH adjustment (preferably 6 to 8), and phosphate buffer to maintain pH. Also included may be a preservative, a humectant, a flavor, and a color.

A pharmaceutically acceptable liquid oral dosage form containing salts of TNCA may also be prepared as a combination solution/suspension, in which a portion of the TNCA salt is dissolved and the remainder is suspended. The preparation may contain 15–1000 mg of TNCA per ml as the salts of lysine, arginine, triethanolamine, piperidine or ammonium hydroxide. The body of the preparation may consist of distilled deionized water into which a portion of the salt is dissolved, and a water-miscible vehicle which is used as the supporting medium for the suspended TNCA salt. This formulation would also contain sodium chloride, sodium hydroxide, and a phosphate buffer as well as a suspending agent, a flavor, and a color.

Another pharmaceutically acceptable liquid oral dosage form containing TNCA may also be prepared as an emulsion. The preparation may contain 15–1000 mg of TNCA per ml as the salts of lysine, arginine, triethanolamine, piperidine, or ammonium hydroxide. The body of the preparation may consist of distilled deionized water and a vegetable oil properly emulsified with an emulsifying agent such as lecithin, pluronics, tweens, brijs, or arlacels, etc., as needed to produce a stable W/O emulsion of the water solution of the TNCA salt in the external oil phase. Also included may be sodium chloride, sodium hydroxide, phosphate buffer, preservative, humectant, flavor and color.

Liquid oral dosage forms may offer advantages in certain patients and in certain applications. Patients unable to swallow large solid dosage forms would be particularly good candidates for a liquid dosage form. Liquid dosage forms may also allow larger amounts of drug to be administered in a manner that promotes patient compliance.

It is also contemplated that a liquid dosage form may be used parenterally (by injection) either by I.V., S.C. or I.M. In the case of an injectable or parenteral liquid dosage form, one ml of solution may contain, in part, 15–1000 mg of TNCA as the salt of lysine, arginine, triethanolamine, piperidine, and/or ammonium hydroxide with lysine, arginine and ammonium being preferred. Also contained in the solution would be a salt such as sodium chloride for the purpose of achieving isotonicity; sodium hydroxide for adjustment of pH as needed (preferably to within the range 6–8); phosphate buffer; a preservative if needed; and U.S. Pat. Water for Injection.

EXAMPLE 9

| Injectable (IV, IM, SC) - Single Dose Ampule or Vial | |
| --- | --- |
| TNCA | 15–1000 mg. |
| Base* | stoichiometric equivalent weight in mg. |
| Sodium chloride | (1) |
| Sodium hydroxide | (2) |
| Phosphate buffer | (3) |
| Water for injection, U.S.P., q.s.a.d. | 1 ml |

EXAMPLE 10

| Injectable (IV, IM, SC) - Multiple Dose Vial | |
| --- | --- |
| TNCA | 15–1000 mg |
| Base* | stoichiometric equivalent weight in mg. |
| Sodium chloride | (1) |
| Sodium hydroxide | (2) |
| Phosphate Buffer | (3) |
| Water for injection, U.S.P., q.s.a.d. | 1 ml |

(1) Sufficient to achieve isotonicity and maintain constant ionic strength.
(2) Sufficient to adjust pH to 7.0 ± 2.
(3) Sufficient to maintain pH at 7.0 ± 2.
(4) e.g., thimerosol, benzyl alcohol, etc., to prevent multiple withdrawal microbial contamination.

EXAMPLE 11

| Oral Solution | |
| --- | --- |
| TNCA | 15–1000 mg |
| Base* | equivalent weight in mg. |
| Sodium chloride | (1) |
| Sodium hydroxide | (2) |
| Phosphate Buffer | (3) |
| Preservative | (4) |
| Humectant | (5) |
| Flavor | (6) |
| Color | (7) |
| Distilled deionized water, U.S.P., q.s.a.d. | 1 ml |

(1) Sufficient to maintain constant ionic strength
(2) Sufficient to adjust pH to 7.0 ± 2.
(3) Sufficient to maintain pH to 7.0 ± 2.
(4) e.g., benzyl alcohol, potassium sorbate, methyl and propyl parabens, either alone or in combination; to prevent microbial contamination.
(5) e.g., glycerine, propylene glycol, polyethylene glycol 100 to 1000, either alone or in combination; to prevent evaporation and subsequent crystal growth and/or caplock.
(6) e.g., artificial or natural flavor extracts or solutions, aspartame, saccharin, dextrose, or sucrose; to impart an esthetically acceptable taste.
(7) Water-soluble colorants to impart a desired tint.

EXAMPLE 12

| Oral Combination Solution/Suspension | |
| --- | --- |
| TNCA | 15–1000 mg. |
| Base* | stoichiometric equivalent weight in mg. |
| Sodium chloride | (1) |
| Sodium hydroxide | (2) |
| Phosphate buffer | (3) |
| Preservative | (4) |
| Humectant | (5) |
| Flavor | (6) |
| Color | (7) |
| Suspending agent | (8) |
| Distilled deionized water | X |
| Water - miscible liquid vehicle 100 − X | (9) q.s.a.d. 1 ml |

(1) Sufficient to maintain constant ionic strength
(2) Sufficient to adjust pH to 7.0 ± 2.
(3) Sufficient to maintain pH to 7.0 ± 2.
(4) e.g., benzyl alcohol, potassium sorbate, methyl and propyl parabens, either alone or in combination; to prevent microbial contamination.
(5) e.g., glycerine, propylene glycol, polyethylene glycol 100 to 1000, either alone or in combination; to prevent evaporation and subsequent crystal growth and/or caplock.
(6) e.g., artificial or natural flavor extracts or solutions, aspartame, saccharin, dextrose, or sucrose; to impart an esthetically acceptable taste.
(7) Water-soluble colorants to impart a desired tint.
(8) e.g., methocel, sodium carboxymethyl cellulose, hydroxypropyl cellulose, keltrol, acacia, etc., to provide an easily re-dispersable stable suspension.
(9) Chosen from the humectant group but present in significantly larger quantities so that the amount of TNCA salt present in excess of its solubility in water is suspended in the combination vehicle.

EXAMPLE 13

| Oral Combination Solution/Emulsion | |
| --- | --- |
| TNCA | 15–1000 mg. |
| Base* | stoichiometric equivalent weight in mg. |
| Sodium Chloride | (1) |
| Sodium Hydroxide | (2) |
| Phosphate Buffer | (3) |
| Preservative | (4) |
| Humectant | (5) |
| Flavor | (6) |
| Color | (7) |
| Emulsifying Agent | (8) |
| Distilled Deionized Water | X |

| Oral Combination Solution/Emulsion | | |
|---|---|---|
| Vegetable Oil 100 − X | (9) q.s.a.d. 1 ml | |

(1) Sufficient to maintain constant ionic strength
(2) Sufficient to adjust pH to 7.0 ± 2.
(3) Sufficient to maintain pH to 7.0 ± 2.
(4) e.g., benzyl alcohol, potassium sorbate, methyl and propyl parabens, either alone or in combination; to prevent microbial contamination.
(5) e.g., glycerine, propylene glycol, polyethylene glycol 100 to 1000, either alone or in combination; to prevent evaporation and subsequent crystal growth and/or caplock.
(6) e.g., artificial or natural flavor extracts or solutions, aspartame, saccharin, dextrose, or sucrose; to impart an esthetically acceptable taste.
(7) Water - soluble colorants to impart a desired tint.
(8) e.g., lecithin, pluoronics, tweens, brijs, arlacels, etc; to produce a stable w/o emulsion of the water solution of TNLY in the external oil phase.
(9) e.g., peanut oil, corn oil, safflower oil; to function as the external phase of the water in oil emulsion.
*Base is selected from the class of lysine, arginine, ammonium hydroxide, piperidine and triethanolamine.

The following are specific exemplifications within the formulations of Examples 9 to 12.

EXAMPLE 14

| Injectable (I.V., I.M., S.C.) - Single Dose | |
|---|---|
| TNCA | 400 mg |
| l-lysine | 328 mg |
| sodium chloride, U.S.P. | 5 mg |
| sodium hydroxide, U.S.P. | 0.1 mg |
| phosphate buffer (pH 7.0) | 0.5 ml |
| water for injection, U.S.P. q.s.a.d. | 5.0 ml |

EXAMPLE 15

| Injectable - Multiple Dose | |
|---|---|
| TNCA | 400 mg |
| l-lysine | 328 mg |
| sodium chloride, U.S.P. | 5 mg |
| sodium hydroxide, U.S.P. | 0.1 mg |
| phosphate buffer (pH 7.0) | 0.5 ml |
| Thimerosol | 0.05 mg |
| water for injection, U.S.P. q.s.a.d. | 5.0 ml |

EXAMPLE 16

| Oral Solution | |
|---|---|
| TNCA | 600 mg |
| l-arginine | 586.5 mg |
| sodium chloride, U.S.P. | 2.0 mg |
| sodium hydroxide, U.S.P. | 0.2 mg |
| potassium sorbate, U.S.P. | 0.05 mg |
| phosphate buffer (pH 7.0) | 3.0 ml |
| glycerine, U.S.P. | 100 mg |
| saccharin sodium, U.S.P. | 0.5 mg |
| natural strawberry flavor | 0.05 ml |
| FD & C Red #40 | 0.0001 mg |
| distilled deionized water q.s.a.d. | 10.0 ml |

EXAMPLE 17

| Oral Combination Solution/Suspension | |
|---|---|
| TNCA | 1000 mg |
| triethanolamine | 420 mg |
| sodium chloride, U.S.P. | 3.0 mg |
| sodium hydroxide, U.S.P. | 0.3 mg |
| phosphate buffer (pH 7.0) | 5.0 ml |
| saccharin sodium | 0.7 mg |
| natural cherry flavor | 0.05 ml |
| FD & C Red #2 | 0.0001 mg |
| methyl paraben | 0.004 mg |
| propyl paraben | 0.001 mg |
| sodium carboxymethylcellulose | 0.5 mg |
| propylene glycol | 7.5 ml |
| distilled deionized water q.s.a.d. | 15.0 ml |

EXAMPLE 18

| Oral Combination Solution/Emulsion | |
|---|---|
| TNCA | 300 mg |
| Ammonium hydroxide, U.S.P. 28% | 2.1 ml |
| sodium chloride, U.S.P. | 1.0 mg |
| sodium hydroxide, U.S.P. | 0.1 mg |
| potassium sorbate, U.S.P. | 0.025 mg |
| polyethylene glycol 400 | 10.0 mg |
| phosphate buffer (pH 7.0) | 1.0 ml |
| saccharin sodium, U.S.P. | 0.1 mg |
| natural banana flavor | 0.02 ml |
| FD & C yellow #6 | 0.0005 mg |
| peanut oil | 3.5 ml |
| distilled deionized water q.s.a.d. | 5.0 ml |

We claim:

1. A water-soluble compound selected from the group consisting of the lysine and arginine salts of thionapthene-2-carboxylic acid (TNCA).

2. A compound as defined in claim 1 wherein the salt is a lysine salt.

3. A compound as defined in claim 1 wherein the salt is an arginine salt.

* * * * *